(12) United States Patent
Bronkalla et al.

(10) Patent No.: US 10,741,283 B2
(45) Date of Patent: Aug. 11, 2020

(54) ATLAS BASED PRIOR RELEVANCY AND RELEVANCY MODEL

(71) Applicant: INTERNATIONAL BUSINESS MACHINES CORPORATION, Armonk, NY (US)

(72) Inventors: Mark Bronkalla, Hartland, WI (US); Amy Chenault, Cambridge, MA (US); James Thompson, San Diego, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 520 days.

(21) Appl. No.: 15/257,849

(22) Filed: Sep. 6, 2016

(65) Prior Publication Data

US 2018/0068079 A1    Mar. 8, 2018

(51) Int. Cl.
*G16H 40/63* (2018.01)
*G16H 10/20* (2018.01)
*G16H 30/20* (2018.01)

(52) U.S. Cl.
CPC ............. *G16H 40/63* (2018.01); *G16H 10/20* (2018.01); *G16H 30/20* (2018.01)

(58) Field of Classification Search
CPC .................................................... G16H 30/00
See application file for complete search history.

(56) References Cited

U.S. PATENT DOCUMENTS

| | | | |
|---|---|---|---|
| 2008/0046286 A1* | 2/2008 | Halsted | G06Q 50/22 705/2 |
| 2010/0050110 A1* | 2/2010 | Hughes | G06F 19/00 715/781 |
| 2013/0222430 A1* | 8/2013 | Bredno | G06T 7/0014 345/634 |
| 2015/0294467 A1 | 10/2015 | Blumhofer et al. | |
| 2015/0359430 A1 | 12/2015 | Ben-Haim | |
| 2016/0155236 A1* | 6/2016 | Davey | G06T 19/20 382/131 |
| 2016/0171692 A1 | 6/2016 | Blumhofer et al. | |

* cited by examiner

*Primary Examiner* — Sheetal R Paulson
(74) *Attorney, Agent, or Firm* — Erik A. Huestis; Stephen J. Kenny; Foley Hoag, LLP

(57) ABSTRACT

User interfaces for navigating medical studies are provided. In various embodiments, a human avatar having a plurality of selectable regions is displayed. Indications of the presence of prior studies are displayed corresponding to the plurality of selectable regions. A selection of a region of the plurality of selectable regions is received from a user. An indication of one or more prior study is displayed corresponding to the selected region.

20 Claims, 10 Drawing Sheets

ATLAS BASED PRIOR RELEVANCY AND RELEVANCY MODEL

BACKGROUND

Embodiments of the present invention relate to navigating medical studies, and more specifically, to an atlas based prior relevancy and stickman relevancy model.

BRIEF SUMMARY

According to embodiments of the present disclosure, methods of and computer program products for navigating medical studies are provided. A human avatar having a plurality of selectable regions is displayed. Indications of the presence of prior studies are displayed corresponding to the plurality of selectable regions. A selection of a region of the plurality of selectable regions is received from a user. An indication of one or more prior study is displayed corresponding to the selected region.

DETAILED DESCRIPTION

Figure 1:
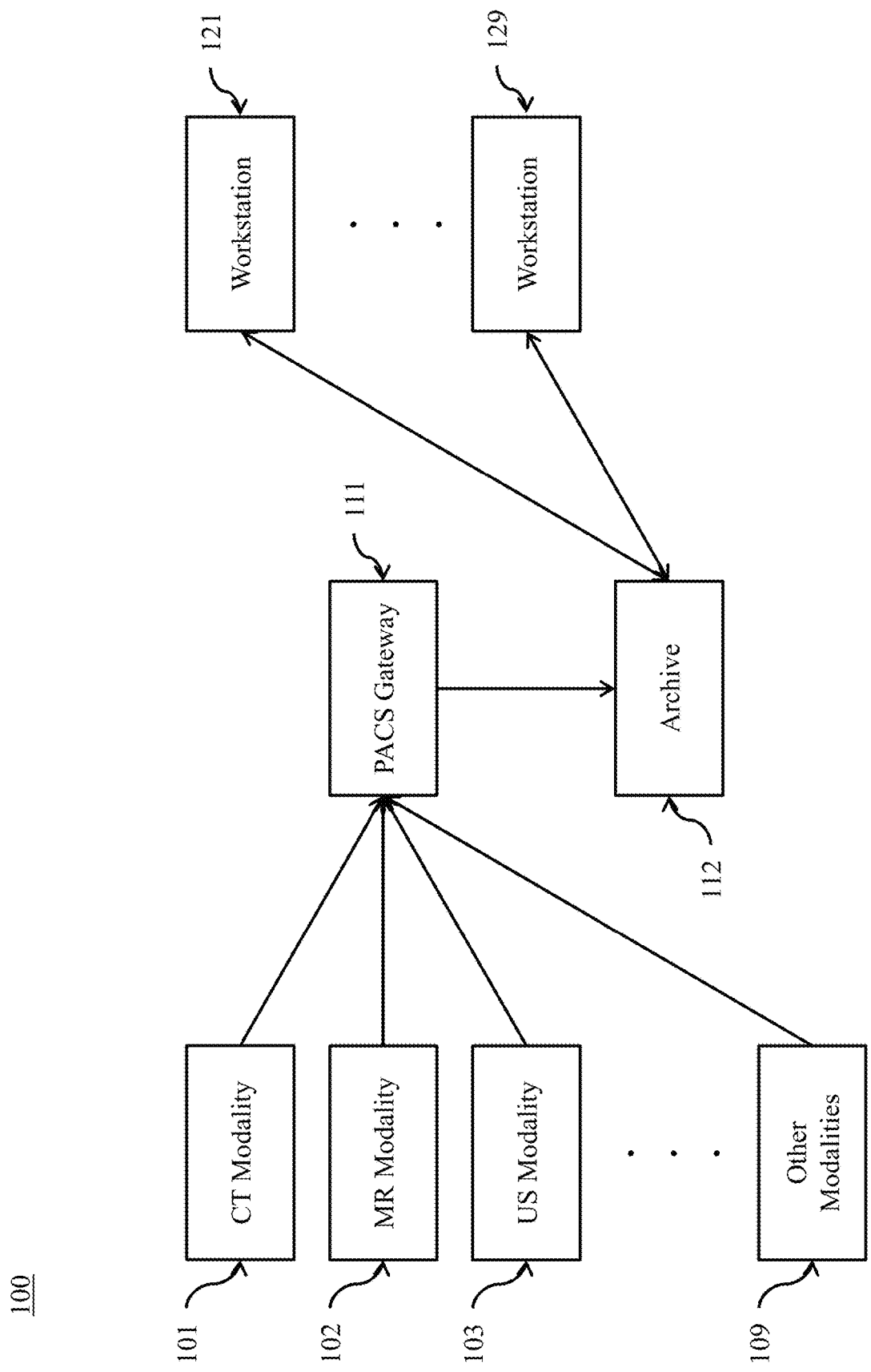
FIG. 1 depicts an exemplary Picture Archiving and Communication System.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

When reading a current imaging study the reader, often a radiologist but sometimes an orthopedic surgeon or other specialist, can obtain important context by seeing relevant prior comparison exams. For example, a wrist or an elbow would be relevant to a forearm. A chest x-ray or MR may be relevant to a shoulder image.

Alternative methods for identifying relevant priors may rely on rules based on the study description, procedure name, or procedure code. However, these values are often vague or varied. For example, relevant priors to a head CT might have names containing brain, orbits, eye, c-spine, etc. Thus, a comprehensive list of rules may be quite long, with many facilities dealing with many thousands of procedure names. This list is ever increasing particularly with inbound referrals from other institutions and as patients bring in their own prior comparison studies. Rule maintenance in such approaches is not real time and may result in delays in selecting the right prior comparison study or result in a study being overlooked.

A reader may wish to obtain more specific comparisons, not just a hip x-ray but one before or after the hip implant. Similarly a reader may be looking for standing or weight bearing images of the knees or hips and disregard those shot in a recumbent position or wheel chair. In certain contexts it may be important to the viewer to find images based on whether they were captured with contrast agents or not. To find this information manually would require opening each study, examining reports, or looking at thumbnail images. However, this is tedious and time consuming, especially when patients may have dozens or hundreds of exams to search through.

To address these and other limitations of alternative approaches, the present disclosure provides graphical tools for browsing prior studies. In particular, in various embodiments, an atlas based prior relevancy and stickman relevancy model is provided. A schematic image opf of the human body is displayed with various indicators as set forth below. The systems and methods laid out herein are particular suitable for radiologists, who are trained to pattern match. Graphical means enable rapid filtering of the lists of dozens or hundreds of studies to a handful.

In various embodiments, a method of taking imaging studies and matching them to anatomical atlases is provided. The atlases contain the locations of the major body parts and organs. These are either registered together or cognitively matched.

The images matched to the atlas are then tagged with the body parts contained within them. This may be at various levels of detail, such as the major bones of the body (e.g., femur or patella), major anatomical features (e.g., orbits or cervical spine), or major organs (e.g., heart, liver, lungs, prostate).

In various embodiments, implants are also recognized and mapped (e.g., hip, knee, shoulder, ankle) as well as temporary devices such as a chemo-port or peripherally inserted central catheter (PICC) line.

In various embodiments, the anatomy of a given study is applied to a schematic human figure, highlighting the anatomy contained in the study or individual images. The implants are applied to the schematic figure as adornments symbolizing their presence. Upright, recumbent or wheelchair type postures can be indicated when they are detected. Major organs may optionally be shown as well. In addition, pregnancy may also be indicated.

In some embodiments, the schematic view of the human body may be described as a stickman or stick figure, although the display may vary between embodiments. The schematic views provide a simple graphical means of visualizing the anatomy in various studies without having to rely on reading text opening the study or a thumbnail or the report.

In some embodiments, a user can indicate how much of the body they want to encompass as relevant priors by clicking on selected stick figure body parts or circling or otherwise selecting a group of parts such as by a mouse swipe over. Additional symbolic items can be shown (e.g., a syringe icon for a contrast study, scale for weight bearing, or a sitting position for wheel chair). The graphical selections may also have textual or tabular representations so that the user is not limited to only the graphical presentation.

In various embodiments, studies are cataloged based on the extent of the coverage of each studies. In some embodiments, studies are tagged with searchable extent information. In some embodiments, study information is stored in a data structure that ties each study to its extent. However, it will be appreciated that various alternative data structures and data stores are suitable for cataloging the anatomical span of coverage according to the present disclosure. Coverage may be catalogued in terms of organs (e.g., liver, spleen, pancreas, right kidney, left kidney) by bone (e.g., left humerus, vertebrae C1, C2, T1, T2). In some embodiments an extent may given in terms of individual vertebrae, while in some embodiments, it may be given in terms of a span (e.g., discrete C1, C2, C3 or a span C1-C3). This provides precise characterization of the anatomy covered in the image.

Alternative methods using only the study description, procedure code or even body part DICOM tag are insufficient as they are too vague and generalized and do not handle the varying range of anatomical coverage that may be present in images of the same procedural description. Using a procedure description and body part that describes the starting point and then the distance measurements within the images (e.g., CT slice spacing) are likewise inadequate due to variation in size of patient (e.g., a basketball player compared to a child having the same study). The anatomy covered per slice will be quite different. The ability to rapidly tell if a comparison study has the needed anatomical coverage is especially important when working with patients that have large numbers of prior comparison studies. For example while examining the liver, if there are 12 CT chest studies, there is a chance that some may extend their coverage down over the liver. It would be inefficient for a user to open all of the studies and manually scroll to the bottom only to find that the liver is missing or the specific area needed is cut off.

The systems and methods described herein are not limited to radiology and cardiology studies, but are equally applicable to dermatology, pathology eye care and other study types.

In various embodiments, when displaying the schematic view, it is adorned with regional markers that indicate the presence of one or more studies in the anatomical region.

In various embodiments, an anatomical coverage preview is provided for a given study when a user clicks on or hovers over a prior comparison study in a list. A schematic with the coverage for that specific study highlighted may then be highlighted.

In various embodiments, the schematic view varies in size and detail such that it covers the anatomy pertinent for the currently selected study. In some embodiments, this variation is based on user role or type and the current study. For example, a head and neck may be displayed for a neuro study, a skeleton may be displayed for an orthopedic or MSK study, or blood vessels and a heart may be displayed for a cardiac or vascular study.

When there are multiple acquisition devices for the same anatomical region, as is common in eye care, the schematic view (which may be limited to the eye region) can be adorned by graphical features indicating what type of study or image objects are present for a given study or what light spectra are used for the images.

The systems and methods of the present disclosure are not limited to imaging studies but can be used for other study types with localized stimulus, results or specimens. This includes EMG studies, pathology slides and biopsy specimens, and their results.

In various embodiments, coverage between the types (e.g., vessels, organs, bones) is converted based on table look-up or cognitive inference.

When there are incidental findings that require follow-up (e.g., lung nodule seen on a cardiac CT), these can be displayed as adornments of the schematic view, including whether they have been followed up on or not. Follow-up may be via rules based or cognitive based interrogation of the EMR, RIS and other systems.

Referring to FIG. 1, an exemplary PACS 100 consists of four major components. Various imaging modalities 101 . . . 109 such as computed tomography (CT) 101, magnetic resonance imaging (MRI) 102, or ultrasound (US) 103 provide imagery to the system. In some implementations, imagery is transmitted to a PACS Gateway 111, before being stored in archive 112. Archive 112 provides for the storage and retrieval of images and reports. Workstations 121 . . . 129 provide for interpreting and reviewing images in archive 112. In some embodiments, a secured network is used for the transmission of patient information between the components of the system. In some embodiments, workstations 121 . . . 129 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 111 comprises a quality assurance (QA) workstation. The QA workstation provides a checkpoint to make sure patient demographics are correct as well as other important attributes of a study. If the study information is correct the images are passed to the archive 112 for storage. The central storage device, archive 112, stores images and in some implementations, reports, measurements and other information that resides with the images.

Once images are stored to archive 112, they may be accessed from reading workstations 121 . . . 129. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 121 . . . 129 to burn patient studies for distribution to patients or referring physicians.

In some implementations, a PACS includes web-based interfaces for workstations 121 . . . 129. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 2:
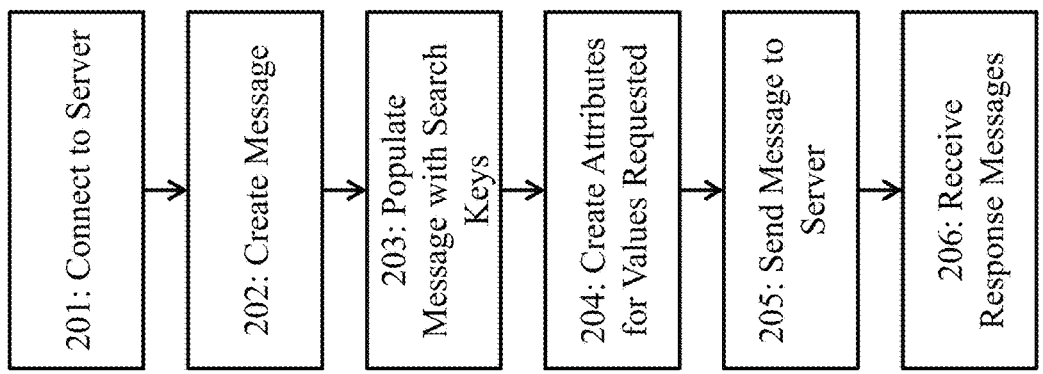
FIG. 2 illustrates an exemplary clinical image search and retrieval method.

Referring to FIG. 2, an exemplary PACS image search and retrieval method 200 is depicted. Communication with a PACS server, such as archive 112, is done through DICOM messages that that contain attributes tailored to each request. At 201, a client, such as workstation 121, establishes a network connection to a PACS server. At 202, the client prepares a DICOM message, which may be a C-FIND, C-MOVE, C-GET, or C-STORE request. At 203, the client fills in the DICOM message with the keys that should be matched. For example, to search by patient ID, a patient ID attribute is included. At 204, the client creates empty attributes for all the values that are being requested from the server. For example, if the client is requesting an image ID suitable for future retrieval of an image, it include an empty attribute for an image ID in the message. At 205, the client send the message to the server. At 206, the server sends back to the client a list of one or more response messages, each of which includes a list of DICOM attributes, populated with values for each match.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

Figure 3:
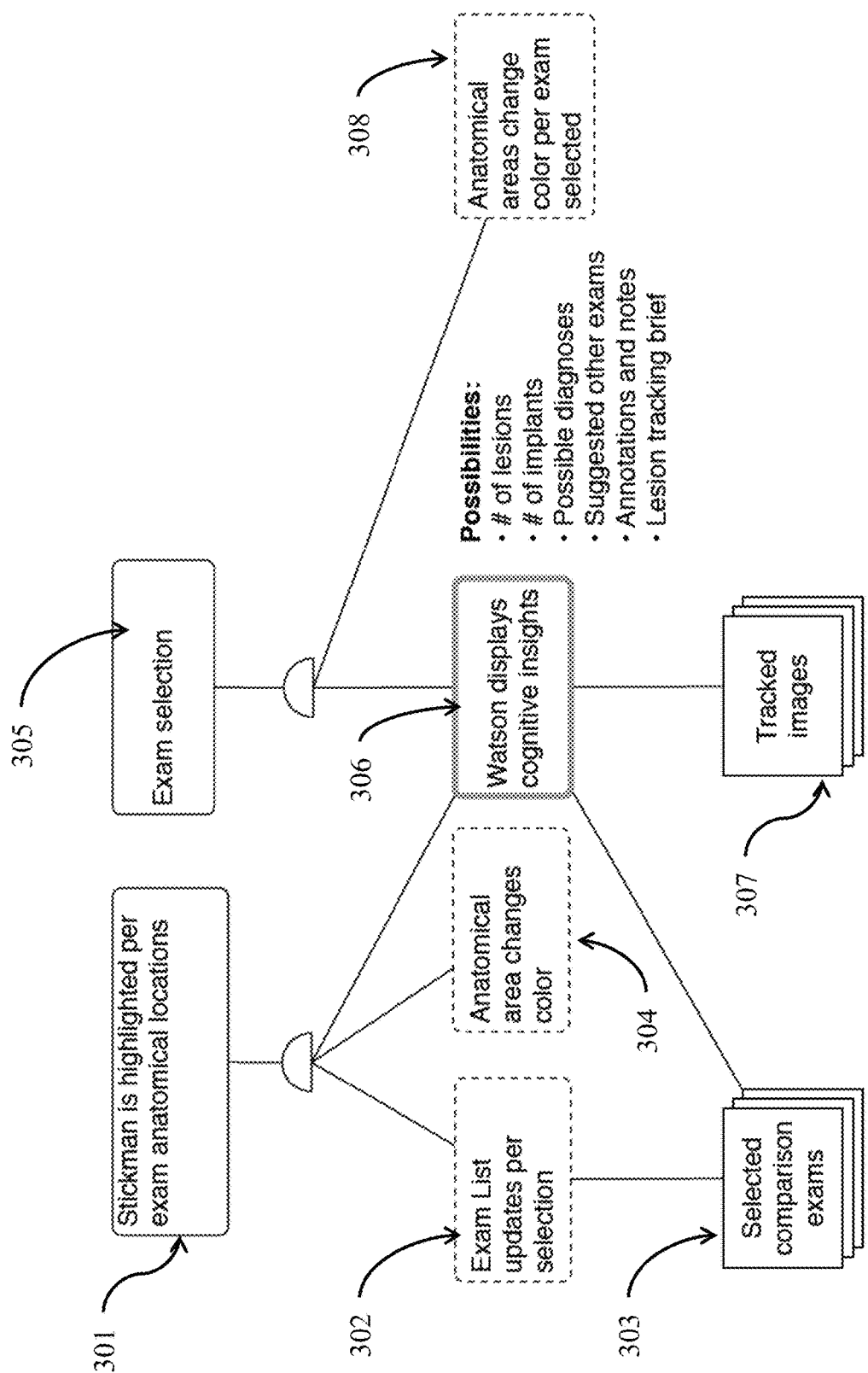
FIG. 3 is a feature map of a system according to embodiments of the present disclosure

Referring now to FIG. 3, a feature map is provided of a system according to embodiments of the present disclosure. In some embodiments, a schematic view, or stickman, is highlighted according to the selected anatomical locations or available exams (301). An examination list is updated per the selection (302). Individual comparison exams may be selected (303, 305). In some embodiments, the color of the anatomical areas of the schematic are updated according to the selected anatomical locations or available exams (304, 308). In some embodiments, the schematic view is supplemented with cognitive insights into the underlying imagery, such as through application of the Watson system (306). In some embodiments, additional indicators are presented with the schematic view, including a number of lesions, a number of implants, a possible diagnosis, suggested additional exams, annotations and notes, or lesion tracking briefs.

Figure 4:
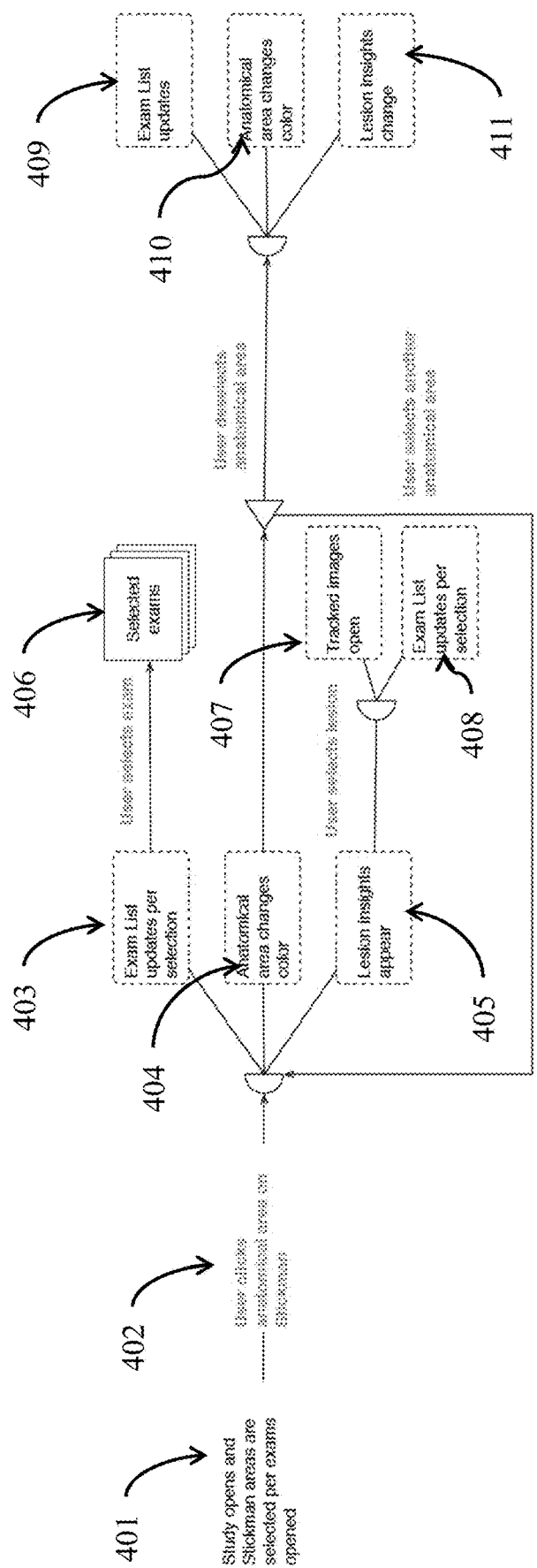
FIG. 4 is an exemplary user flow according to embodiments of the present disclosure

Referring to FIG. 4, an exemplary user flow is provided according to embodiments of the present disclosure. At 401, a study opens and regions in the schematic view, or stickman, are selected according to the exams opened. At 402, a user clicks on an anatomical are in the schematic view. At 403, an exam list updates according to the selection. At 404, the anatomical area changes color according to the selection. At 404, lesion insights are displayed according to the selection. At 406, after a user selects an exam from the list, the exam is opened. At 407, after the user selects a lesion, tracked images are opened based on the legion. At 408, the exam list is updated according to the lesion selection. At

409, after a user deselects an anatomical area, the exam list is updated according to the deselection. At 410, the anatomical area changes color according to the deselection. At 411, the lesion insights change according to the deselection.

Figure 5A:
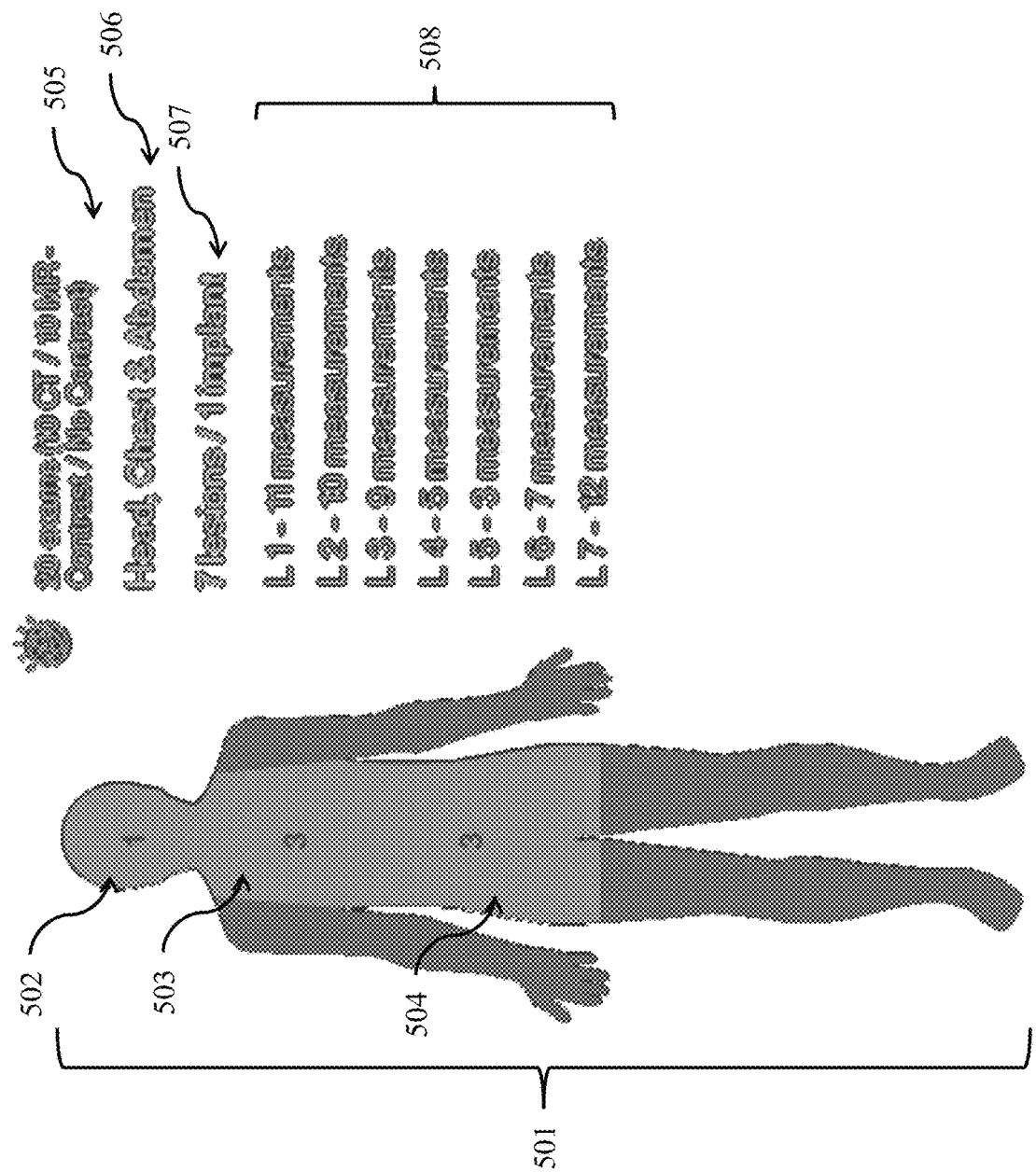
FIG. 5A-B depicts an exemplary schematic view, or stickman, according to embodiments of the present disclosure.
Figure 5B:
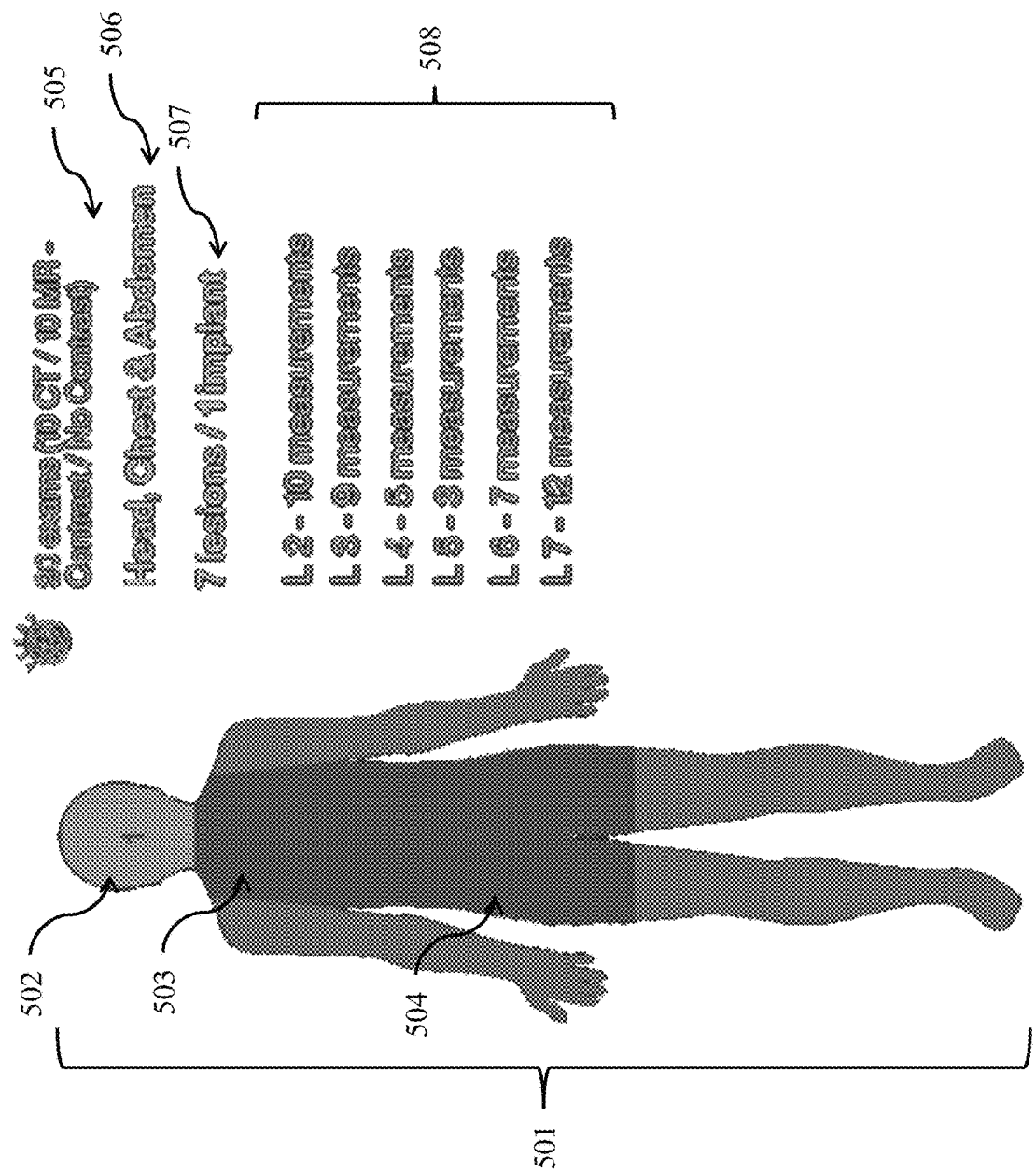

Referring to FIGS. 5A-B, an exemplary schematic view, or stickman, is shown according to embodiments of the present disclosure. Schematic view 501 provides an outline of the human body. Selectable regions 502 . . . 504 allow a user to designate anatomical area of interest. Each region contains a numeric indication of the number of prior studies covering that region. The number of exams is indicated at 505, the regions in which the exams appear is indicated at 506, and the number of lesions and implants is indicated at 507. In addition, the studies available in the selected regions are displayed at 508. In various embodiments, each element is hyperlinked, allowing opening and display of relevant study information. In FIG. 5A, no particular regions are selected, and so information for the head, chest, and abdomen is displayed. In FIG. 5B, the chest and abdomen are selected, and list of studies 508 is updated accordingly. It will be appreciated that alternative divisions of the schematic view may be provided according to embodiments of the present disclosure. For example, left and right abdomen may be separately selectable in some embodiments. Likewise, left and right arms, left and right feet, left and right legs, etc. may be separately selectable. In this way, the user may me certain of laterality of a given study.

Figure 6A:
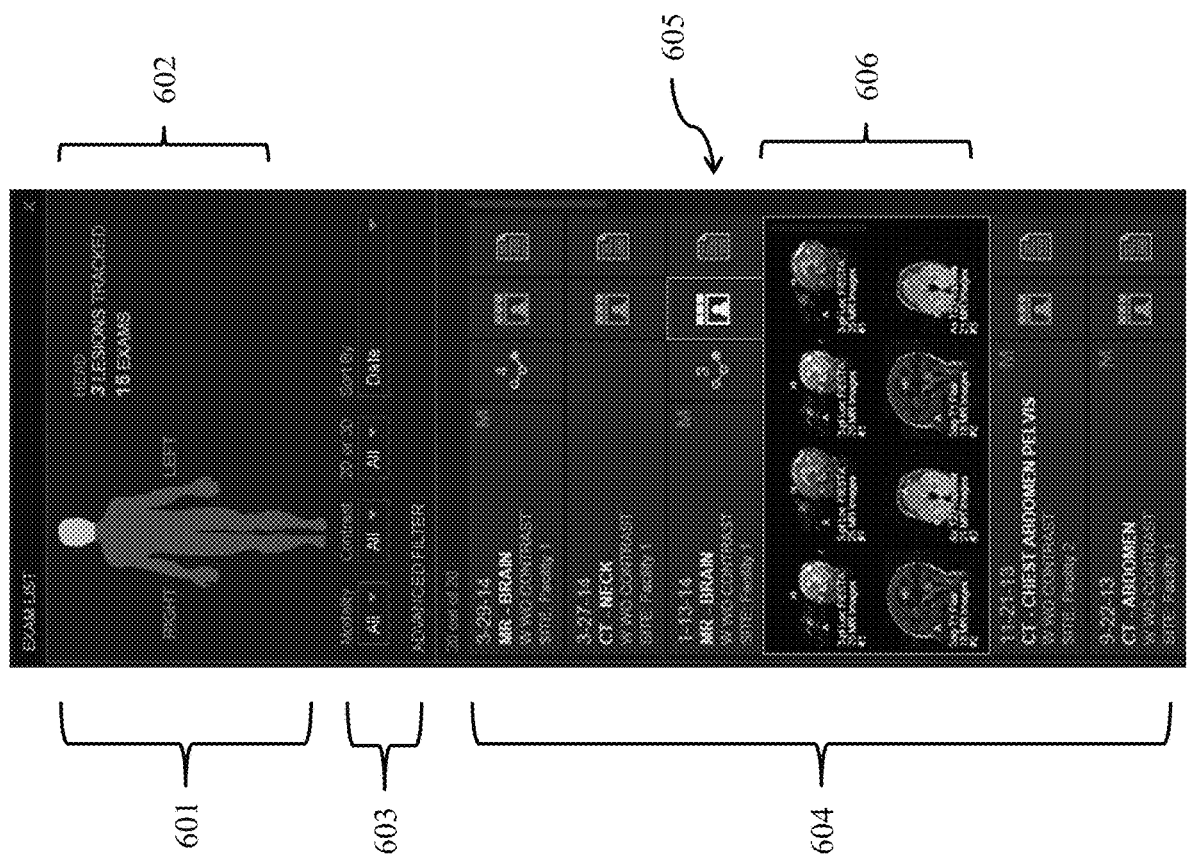
FIG. 6A-B depicts an exemplary schematic view, or stickman, according to embodiments of the present disclosure.
Figure 6B:
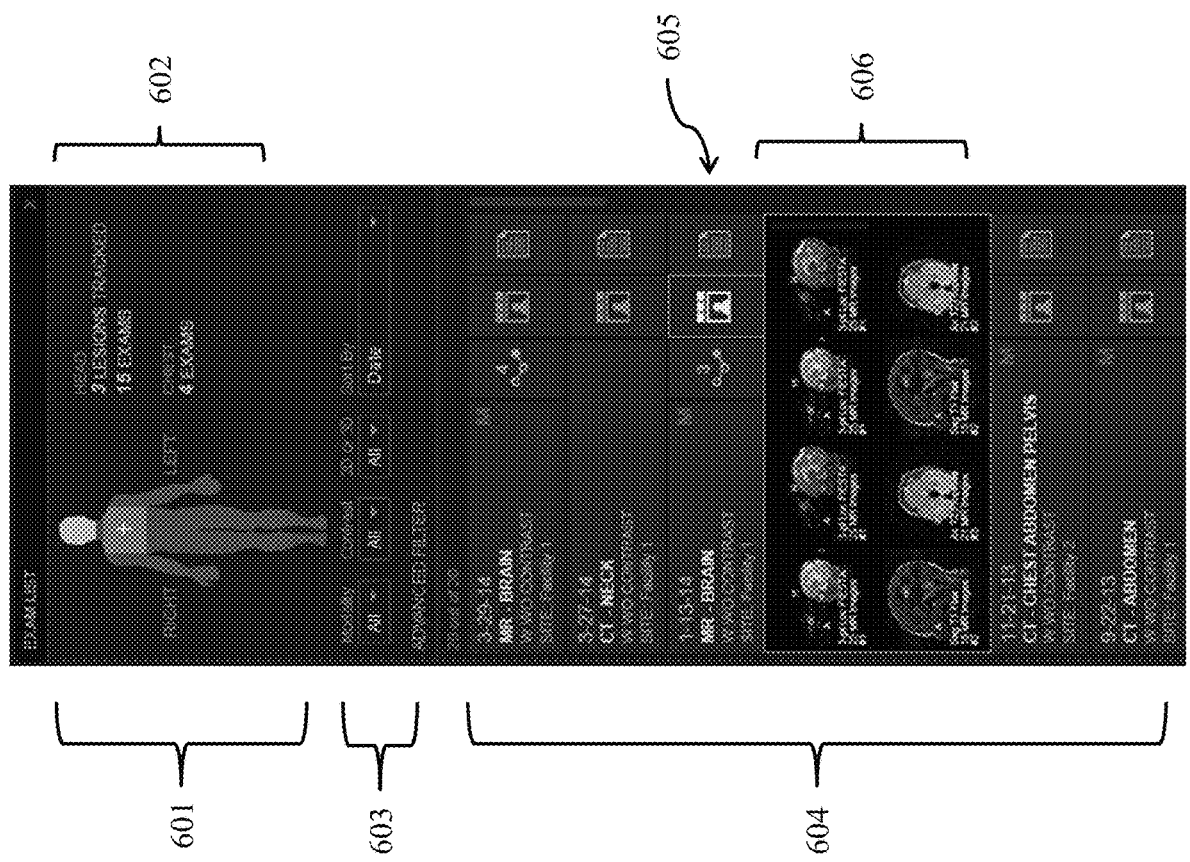

Referring to FIGS. 6A-B, an exemplary schematic view, or stickman, is shown according to embodiments of the present disclosure. Schematic view 601 provides an outline of the human body. In FIG. 6A, only the head is selected, while in FIG. 6B, the head and chest are selected. In some embodiments, a default selection is determined based on a current study. The study count and lesion count is displayed at 602 according to the selection. In various other embodiments, additional information based on the selection may also be displayed. In various embodiments, lesion information is hyperlinked to open a track chart. In various embodiments, filters 603 are provided to enable a user to further select the contents of the study list 604. In some embodiments, filtering may be selected on the basis of modality, contrast, 2D or 3D, date, site or facility name, whether data is available online, or whether a study includes measurements. In addition, filtering may be selected on the basis of laterality of a study. Images of the right and left sides of the body are easily mistaken for one another during interpretation, because the body is substantially symmetrical. Accordingly, by filtering on laterality, mistaken laterality and consequent mistakes can be eliminated.

In some embodiments, studies in the list 604 include a preview button 605, which allows a user to access thumbnails 606 of each study.

Figure 7:
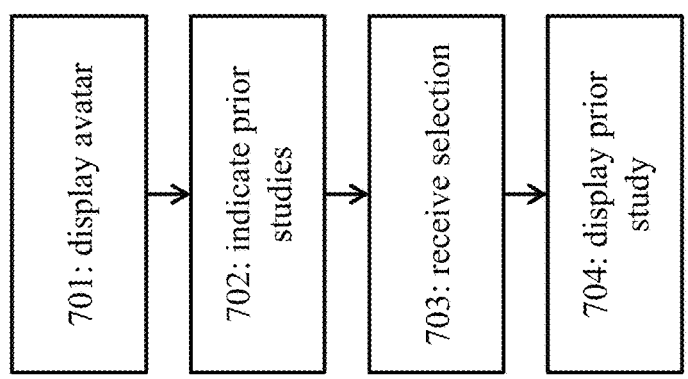
FIG. 7 illustrates a method for navigating medical studies according to embodiments of the present disclosure.

Referring to FIG. 7, a method of navigating medical studies is illustrated according to embodiments of the present disclosure. At 701, a human avatar having a plurality of selectable regions is displayed. At 702, indications of the presence of prior studies are displayed corresponding to the plurality of selectable regions. At 703, a selection of a region of the plurality of selectable regions is received from a user. At 704, an indication of one or more prior study is displayed corresponding to the selected region.

Figure 8:
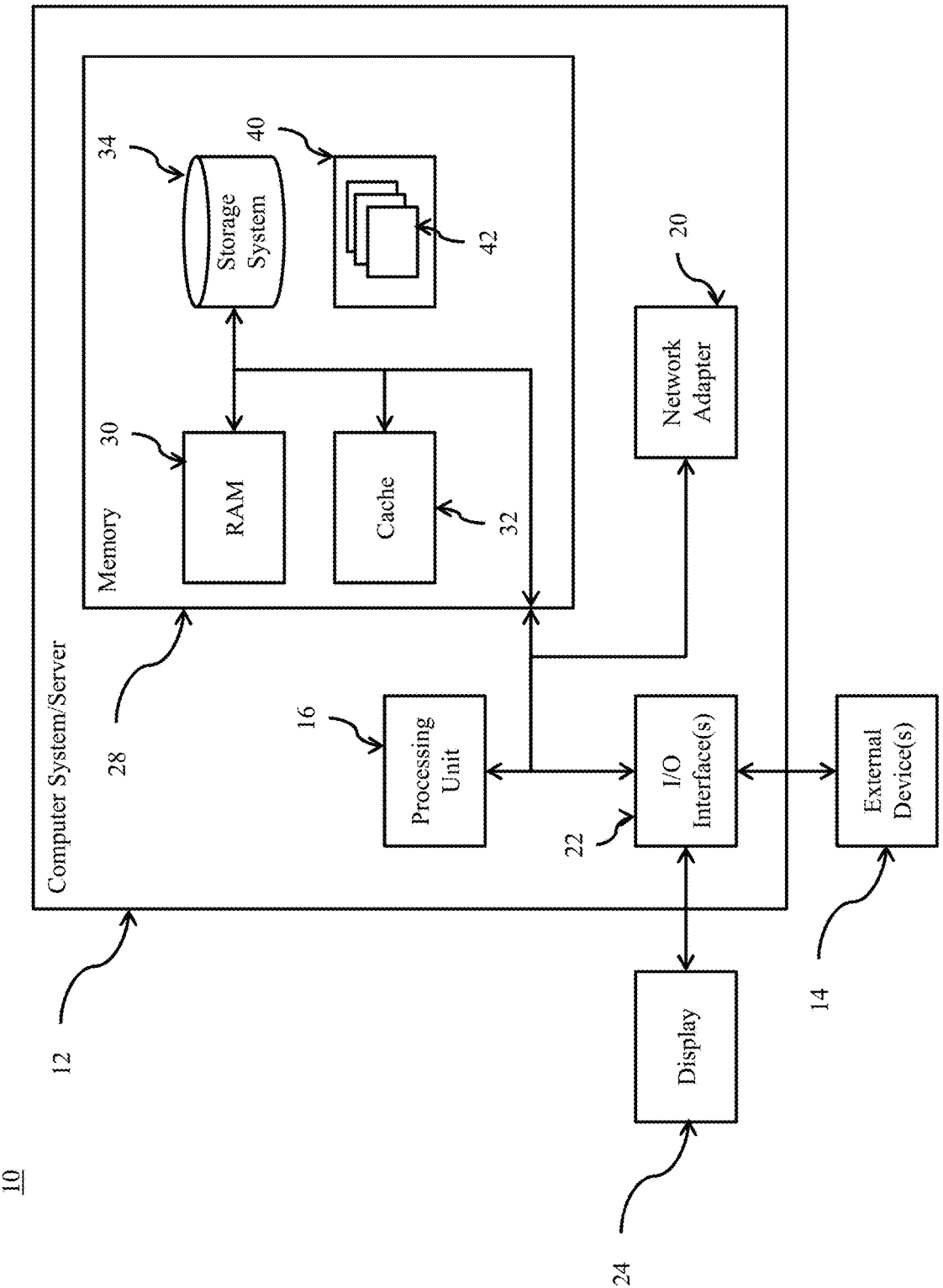
FIG. 8 depicts a computing node according to an embodiment of the present invention.

Referring now to FIG. 8, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    displaying a human avatar having a plurality of selectable regions;
    reading a first prior study received from a remote server, the first prior study relating to one or more of the selectable regions;
    displaying a first indication that the one or more of the selectable regions in the human avatar is selected based on the reading;
    displaying a summary of a first plurality of additional prior studies corresponding to the one or more of the selectable regions;
    displaying a second indication of the presence of a second plurality of additional prior studies corresponding to those of the plurality of selectable regions other than the one or more of the selectable regions;
    receiving from a user a selection of a region of the plurality of selectable regions other than the one or more of the selectable regions;
    after receiving the user selection, updating the display of the summary with one or more of the second plurality of additional prior studies corresponding to the user-selected region thereby displaying, in the summary, the first plurality of additional prior studies and one or more of the second plurality of additional prior studies.

2. The method of claim 1, further comprising:
    receiving from a user one or more filter criteria, the second indication of the second plurality of additional prior studies conforming to the one or more filter criteria.

3. The method of claim 2, wherein the filter criteria comprise the presence of contrast in a prior study.

4. The method of claim 2, wherein the filter criteria comprise the presence of an implant.

5. The method of claim 2, wherein the filter criteria comprise the presence of an organ.

6. The method of claim 2, wherein the filter criteria comprise an indication of laterality.

7. The method of claim 1, wherein the plurality of selectable regions are limited to those overlapping a present study.

8. The method of claim 1, further comprising:
    registering a plurality of prior studies to an anatomical atlas, and thereby assigning each of the plurality of studies to one of the plurality of selectable regions.

9. The method of claim 1, further comprising updating the second indication of the presence of the second plurality of additional prior studies based on the user- selected region.

10. The method of claim 1, wherein the first and second indications include coloring.

11. A computer program product for navigating medical studies, the computer program product comprising a computer readable storage medium having program instructions embodied therewith, the program instructions executable by a processor to cause the processor to perform a method comprising:
    displaying a human avatar having a plurality of selectable regions;
    reading a first prior study received from a remote server, the first prior study relating to one or more of the selectable regions;
    displaying a first indication that the one or more of the selectable regions in the human avatar is selected based on the reading;
    displaying a summary of a first plurality of additional prior studies corresponding to the one or more of the selectable regions;
    displaying a second indication of the presence of a second plurality of additional prior studies corresponding to those of the plurality of selectable regions other than the one or more of the selectable regions;
    receiving from a user a selection of a region of the plurality of selectable regions other than the one or more of the selectable regions;
    after receiving the user selection, updating the display of the summary with one or more of the second plurality of additional prior studies corresponding to the user-selected region thereby displaying, in the summary, the first plurality of additional prior studies and one or more of the second plurality of additional prior studies.

12. The computer program product of claim 11, wherein the method further comprises:
    receiving from a user one or more filter criteria, the second indication of the second plurality of additional prior studies conforming to the one or more filter criteria.

13. The computer program product of claim 12, wherein the filter criteria comprise the presence of contrast in a prior study.

14. The computer program product of claim 12, wherein the filter criteria comprise the presence of an implant.

15. The computer program product of claim 12, wherein the filter criteria comprise the presence of an organ.

16. The computer program product of claim 12, wherein the filter criteria comprise an indication of laterality.

17. The computer program product of claim 11, wherein the plurality of selectable regions are limited to those overlapping a present study.

18. The computer program product of claim 11, wherein the method further comprises:
   registering a plurality of prior studies to an anatomical atlas, and thereby assigning each of the plurality of studies to one of the plurality of selectable regions.

19. The computer program product of claim 11, further comprising updating the second indication of the presence of the second plurality of additional prior studies based on the user-selected region.

20. The computer program product of claim 11, wherein the first and second indications include coloring.

* * * * *